United States Patent
Bird (10) Patent No.: US 9,078,614 B2
(45) Date of Patent: Jul. 14, 2015

(54) LARYNGOSCOPE

(75) Inventor: Ian John Bird, Mitcham (AU)

(73) Assignee: SWIRL TECHNOLOGIES PTY. LTD., Mitcham, Victoria (AU)

(*) Notice: Subject to any disclaimer, the term of this patent is extended or adjusted under 35 U.S.C. 154(b) by 1206 days.

(21) Appl. No.: 12/374,588

(22) PCT Filed: Jun. 22, 2007

(86) PCT No.: PCT/AU2007/000864
§ 371 (c)(1),
(2), (4) Date: Mar. 17, 2010

(87) PCT Pub. No.: WO2007/147211
PCT Pub. Date: Dec. 27, 2007

(65) Prior Publication Data
US 2010/0179387 A1    Jul. 15, 2010

(30) Foreign Application Priority Data

Jun. 20, 2006  (AU) .................................. 2006903330

(51) Int. Cl.
*A61B 1/267*  (2006.01)

(52) U.S. Cl.
CPC ....................................... *A61B 1/267* (2013.01)

(58) Field of Classification Search
USPC ......... 600/185, 188, 190, 191, 193, 197, 199, 600/223, 241, 245; 362/109, 119, 120, 184, 362/197, 199, 287, 249.03, 249.1
See application file for complete search history.

(56) References Cited

U.S. PATENT DOCUMENTS

| | | | |
|---|---|---|---|
| 708,452 A * | 9/1902 | Beist | 604/109 |
| 942,523 A * | 12/1909 | Sawyer | 604/109 |
| 3,638,644 A | 2/1972 | Reick | |
| 3,702,606 A * | 11/1972 | Barnard | 600/220 |
| 4,010,740 A * | 3/1977 | Littorin | 600/220 |
| 4,064,873 A * | 12/1977 | Swenson | 600/215 |
| 4,067,323 A * | 1/1978 | Troutner et al. | 600/223 |
| 4,151,838 A * | 5/1979 | Crew | 600/217 |
| 4,337,761 A | 7/1982 | Upsher | |
| 4,437,458 A | 3/1984 | Upsher | |
| 4,517,964 A | 5/1985 | Upsher | |

(Continued)

FOREIGN PATENT DOCUMENTS

| | | |
|---|---|---|
| GB | 2 209 944 | 6/1989 |
| GB | 2 385 793 | 9/2003 |

OTHER PUBLICATIONS

PCT/AU2007/000864 International Search Report (PCT/ISA/210) dated Aug. 8, 2007.

*Primary Examiner* — Christian Sevilla
(74) *Attorney, Agent, or Firm* — Brinks Gilson & Lione; G. Peters Nichols (57) ABSTRACT

A laryngoscope includes a blade that can be folded outwardly from a storage position to an operative position in which the blade extends from the handle at an angle of the order of 90°. Another laryngoscope includes two blade assemblies that are pivotally mounted together. Each assembly includes a blade and a removable outer sleeve or similar member that protects the blade. The assemblies can be folded outwardly from a storage position to an operative position in which the assemblies extend from each other an angle of the order of 90°. A doctor can remove the outer sleeve from a selected assembly and use the other assembly as a handle of the laryngoscope.

12 Claims, 6 Drawing Sheets

(56) References Cited

U.S. PATENT DOCUMENTS

| | | | |
|---|---|---|---|
| 4,527,553 A | 7/1985 | Upsher | |
| 4,592,343 A | 6/1986 | Upsher | |
| 4,982,729 A * | 1/1991 | Wu | 600/187 |
| 5,060,633 A * | 10/1991 | Gibson | 600/193 |
| 5,065,297 A * | 11/1991 | Santambrogio | 362/413 |
| 5,178,132 A * | 1/1993 | Mahefky | 600/194 |
| 5,355,870 A | 10/1994 | Lacy | |
| 5,462,435 A * | 10/1995 | Young | 433/140 |
| 5,498,231 A * | 3/1996 | Franicevic | 600/190 |
| 5,569,300 A * | 10/1996 | Redmon | 606/207 |
| 5,651,760 A | 7/1997 | Upsher | |
| 5,695,454 A * | 12/1997 | Mourkidou | 600/186 |
| 5,890,793 A * | 4/1999 | Stephens | 362/225 |
| 5,938,591 A | 8/1999 | Minson | |
| 6,004,004 A * | 12/1999 | Altman et al. | 362/191 |
| 6,102,851 A | 8/2000 | Mellin | |
| 2002/0082478 A1 | 6/2002 | McGrath | |
| 2004/0064058 A1* | 4/2004 | McKay | 600/506 |
| 2004/0127770 A1 | 7/2004 | McGrath | |
| 2006/0189847 A1 | 8/2006 | Yee et al. | |

* cited by examiner

LARYNGOSCOPE

This application claims priority to PCT Application No. PCT/AU2007/000864 filed Jun. 20, 2007 published in English on Dec. 27, 2007 as PCT WO 2007/147211 and also to Australian Application No. 2006/903330 filed Jun. 20, 2006, the entire contents of each are incorporated herein by reference.

FIELD OF THE INVENTION

The present invention relates to laryngoscopes.

BACKGROUND

A conventional laryngoscope includes a handle and a disposable "blade" that is releasably mounted to one end of the handle.

The blade is a curved member that is shaped and sized to be inserted into a larynx of a patient through the mouth of the patient and has a light at a forward end that assists a doctor observing the interior of the larynx.

An upper end of the handle and a rear end of the blade are formed as a clip assembly whereby the blade can be clipped onto the handle and retained in an operative position in which the blade extends at an angle of the order of 90° from the handle.

The battery or batteries for the light are conveniently stored in the handle.

Different sized blades are available to suit smaller and larger mouths of patients. Each different sized blade is formed to clip onto a single handle. In use, in situations where a doctor has a handle with no blade clipped onto the handle, the doctor will make an assessment of the required blade size for a particular patient and will then clip the selected blade onto a handle and treat the patient. In use, in situations where a blade is already clipped onto a handle and the blade size is not suitable for a particular patient, the doctor has to unclip the blade from the handle and then clip a new blade onto the handle.

The blades are regarded as single-use members and are disposed of after use.

The handle is a multiple-use member that is used repeatedly with a succession of new blades of the same or different sizes. Typically, the handle is made from stainless steel so that it can survive being used repeatedly.

One important use of laryngoscopes is in crisis situations, for example in emergency rooms in hospitals, where it is necessary for doctors to work quickly to assess patients, with such assessments often requiring the use of laryngoscopes.

In these and other situations, it is desirable for doctors to have convenient access to laryngoscopes that can be used quickly by doctors to minimise delay in assessing patients.

In these and other situations, it is particularly desirable for doctors to have convenient access to multiple-use laryngoscopes that can provide doctors with a plurality of options to use different sized blades without having to spend time replacing an existing blade on a conventional laryngoscope with a different sized blade.

The present invention provides a single use laryngoscope that can be quickly manipulated into an operative position.

The present invention also provides a multiple-use laryngoscope that can be quickly manipulated into an operative position.

DESCRIPTION OF THE INVENTION

According to the present invention there is provided a laryngoscope that includes a handle and a blade that is pivotally mounted to the handle and can be folded outwardly from a storage position in which the blade and the handle are in side by side relationship and extend generally in the same direction and an operative position in which the blade extends from the handle at an angle, typically of the order of 90°.

The above-described pivotal mounting of the handle and the blade means that a doctor can conveniently carry the laryngoscope on his or her person in the storage position and can quickly fold the blade out to the operative position and treat a patient.

Preferably the blade extends at an angle of the order of 90° in the operative position.

The blade may be a replaceable blade.

Preferably the blade is not a replaceable blade so that the laryngoscope is a single use device.

Preferably the blade includes a light in a forward end to assist a doctor observing a patient.

The light of the blade may actuate automatically as the blade assembly is folded outwardly from the storage position to the operative position. The automatic actuation simplifies use of the laryngoscope, and this is particularly important in emergency situations.

In another, although not the only other possible arrangement, the light of the blade may be actuated by a switch on the handle. The switch-actuated light simplifies testing of a light before a laryngoscope leaves a factory. In addition, the switch-actuated light means that the laryngoscope can be used conveniently as a torch when the laryngoscope is in the folded storage position. In addition, the switch-actuated light minimises the possibility of the light being actuated accidentally.

Preferably the blade is curved.

Preferably the laryngoscope includes a hub that defines a pivotal mounting for the blade.

Preferably the hub defines a housing for a battery or batteries for the light of the blade.

According to the present invention there is also provided a laryngoscope that includes two blade assemblies, each assembly including a blade and an outer sleeve or similar member that protects the blade and is removable from the blade, and the assemblies being pivotally connected together at one end of each assembly so that the assemblies can be folded relative to each other from a storage position in which the assemblies are in side by side relationship and extend generally in the same direction and an operative position in which the assemblies extend in different directions.

The above-described laryngoscope provides doctors with a selection of two blades for use in the treatment of patients.

In addition, as is the case for the above-described single blade laryngoscope, the pivotal connection of the blade assemblies means that a doctor can conveniently carry the laryngoscope on his or her person in the storage position and can quickly fold the blade assemblies out to the operative position and treat a patient.

In use, a doctor selects a required blade for a particular patient, folds the blade assemblies outwardly from the storage position to the operative position, removes the sleeve or similar member from the selected blade assembly thereby exposing the blade, grips the other blade assembly as the handle of the laryngoscope, and manipulates the laryngoscope as required to assess the patient.

Preferably the blade assemblies extend at an angle of the order of 90° in the operative position.

Preferably the blade of one of the blade assemblies is larger than the blade of the other blade assembly.

Preferably the outer sleeves or similar members are shaped to define convenient hand grips.

Preferably each blade includes a light in a forward end to assist a doctor observing a patient.

The lights of the blades may actuate automatically as the blade assemblies are folded outwardly from the storage position to the operative position.

In another, although not the only other possible arrangement, the lights of the blades may be actuated by switches on the blades.

Preferably each blade is curved.

Preferably the laryngoscope includes a hub that defines a pivotal mounting for the blade assemblies.

Preferably the hub defines a housing for a battery or batteries for the lights of the blade assemblies.

DESCRIPTION OF THE DRAWINGS

The present invention is described further by way of example with reference to the accompany drawings, of which.

DESCRIPTION OF EMBODIMENTS

Figure 1:
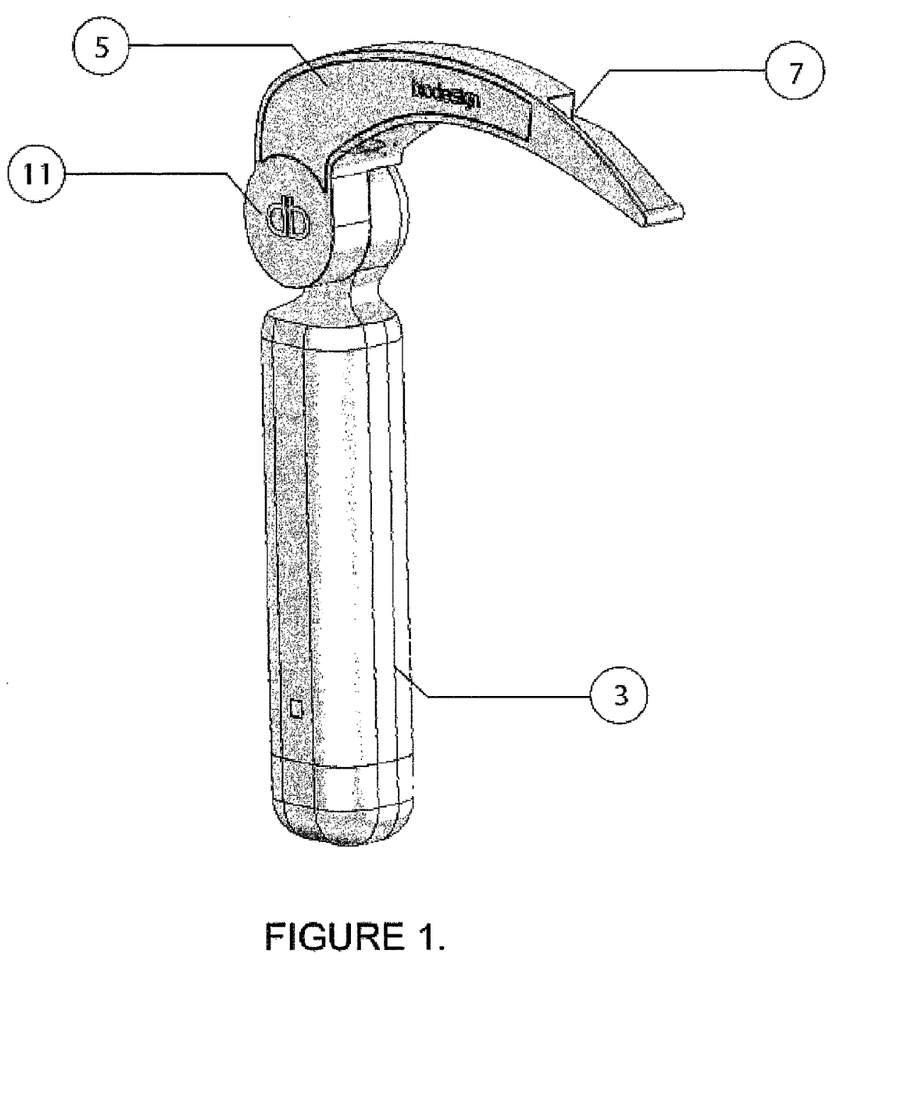
FIG. 1 is a perspective view of one embodiment of a laryngoscope in accordance with the present invention in an operative position.
Figure 2:
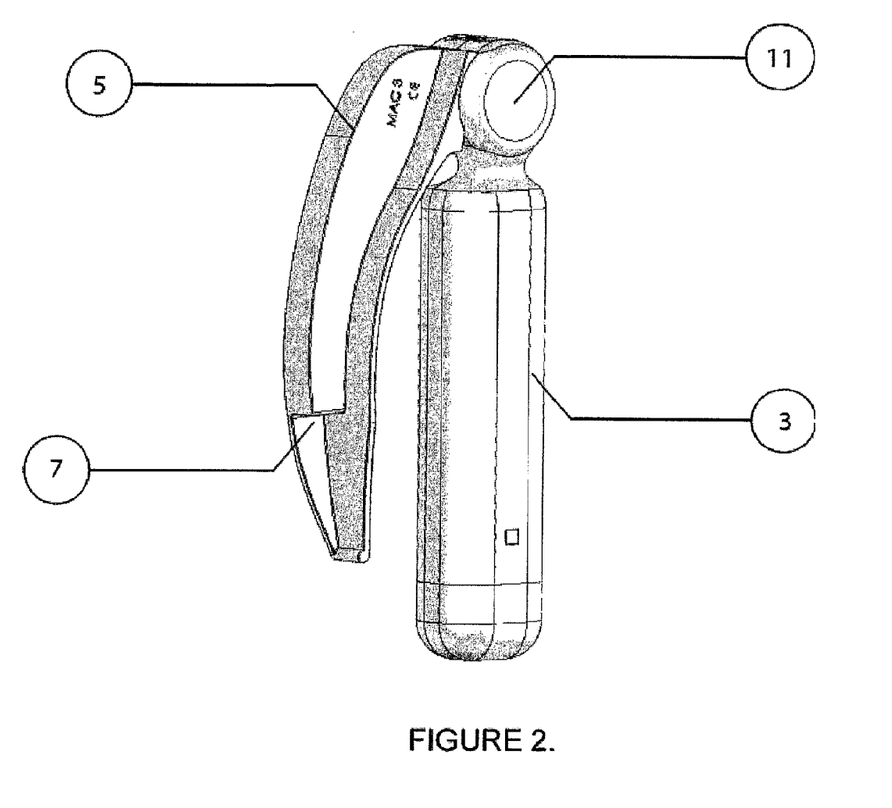
FIG. 2 is a perspective view of the laryngoscope shown in FIG. 1 in a storage position.
Figure 3:
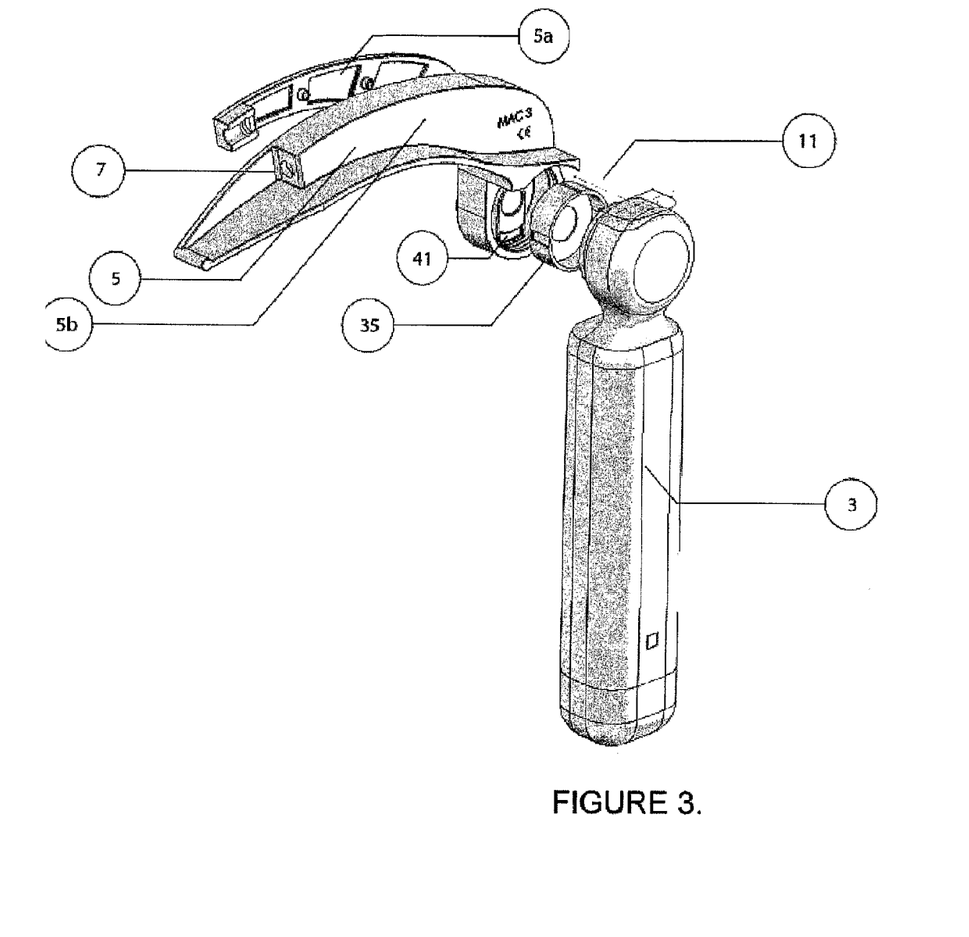
FIG. 3 is an exploded perspective view of the laryngoscope shown in FIG. 1 in the operative position which illustrates the components of the laryngoscope.

The embodiment of the laryngoscope in accordance with the present invention shown in FIGS. 1-3 includes a handle 3 and a disposable blade 5 that is connected to one end of the handle 3 via a hub 11.

The blade 5 is a curved member that is shaped and sized to be inserted into a larynx of a patient through the mouth of the patient and has a light 7 at a forward end to assist a doctor observing the interior of the larynx.

As can best be seen from the exploded perspective view of FIG. 3, the blade 5 is made from two components 5a, 5b that are moulded from a rigid plastics material and are press-fitted together.

The blade 5 is pivotally connected to the handle 3 and can be folded outwardly from (a) a storage position shown in FIG. 2, in which the blade 5 is located against the handle 3 whereby the handle 3 and the blade 5 are in side by side relationship and extend generally in the same direction, to (b) an operative position shown in FIG. 1, in which the blade 5 extends from the handle 3 at an angle of the order of 90°. This pivotal mounting and folding movement between storage and operative positions are key features of the laryngoscope of the present invention.

As can best be seen from the exploded perspective view of FIG. 3, the ends of the blade 5 and the handle 3 that are pivotally connected together are formed to define the hub 11. The hub 11 also includes a cylindrical sleeve 35 that is located between the ends of the blade 5 and the handle 3. The three components are formed to be assembled together as a press fit.

A battery or batteries for powering the light 9 are conveniently stored in the hub 11. Specifically, as can best be seen from FIG. 3, the hub 11 defines a hollow chamber 41 for housing a battery or batteries (not shown).

The laryngoscope is constructed so that the light 7 is actuated automatically as the blade 5 is folded outwardly from the storage position shown in FIG. 2 to the operative position shown in FIG. 1.

Figure 4:
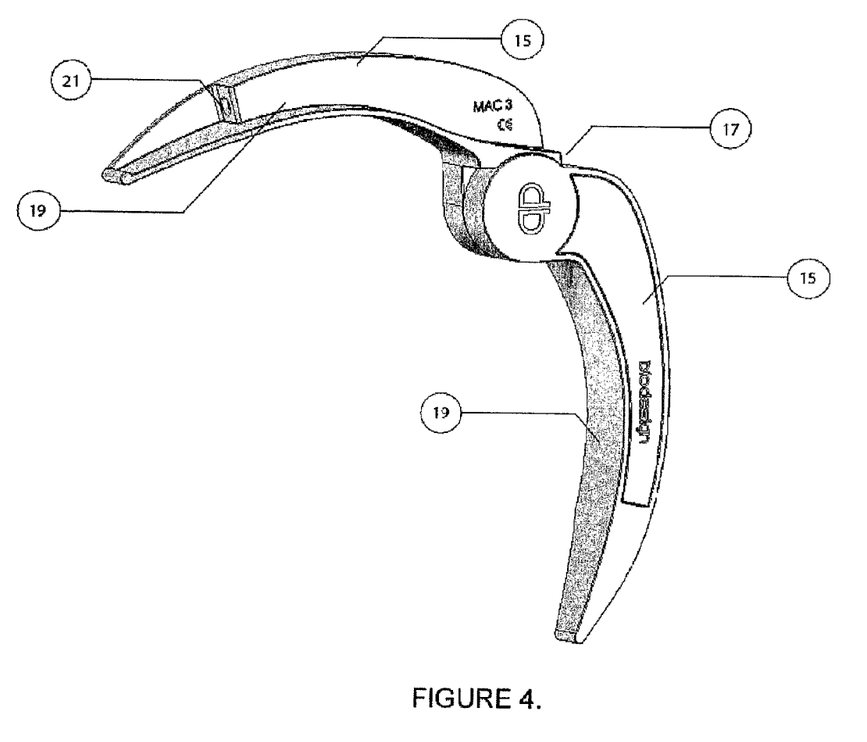
FIG. 4 is a perspective view of another embodiment of a laryngoscope in accordance with the present invention in an operative position.
Figure 5:
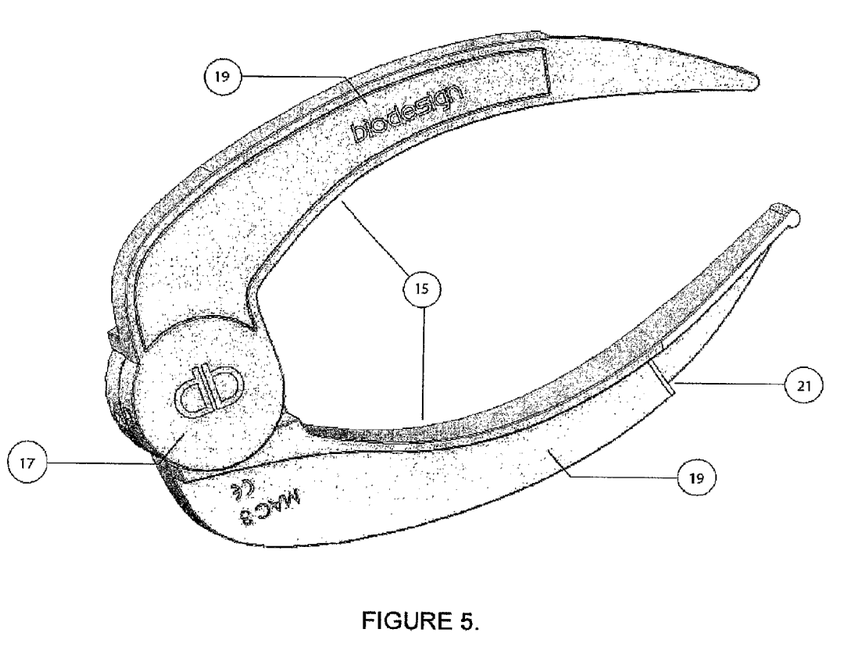
FIG. 5 is a perspective view of the laryngoscope shown in FIG. 4 in a storage position.
Figure 6:
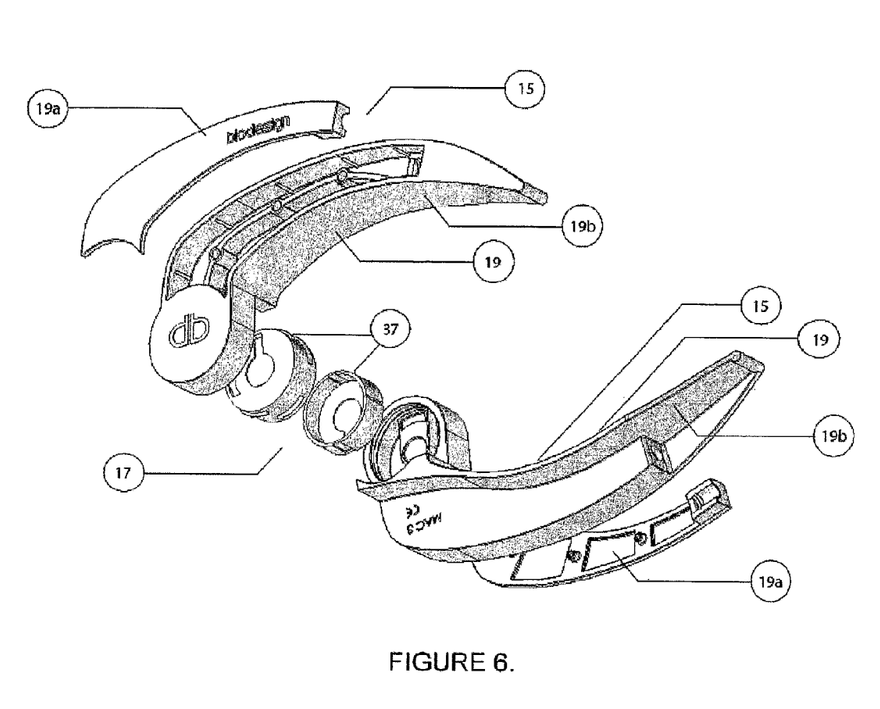
FIG. 6 is an exploded perspective view of the laryngoscope shown in FIG. 5 in the storage position which illustrates the components of the laryngoscope.

The embodiment of the laryngoscope in accordance with the present invention shown in FIGS. 4-6 includes two blade assemblies 15 that are pivotally connected together at one end of each assembly 15 via a hub 17 and can be folded outwardly from the storage position shown in FIG. 5 to the operative position shown in FIG. 4. This pivotal mounting and folding movement between storage and operative positions are key features of the laryngoscope of the present invention.

Each blade assembly 15 includes a blade 19 and an outer sleeve (not shown) positioned on and shielding the blade 19.

The blades 19 are selected to be different sizes, whereby a larger sized blade is suitable particularly for adults and a smaller sized blade is suitable particularly for children.

As can best be seen from the exploded perspective view of FIG. 6, the blade assemblies 19 are each made from two components 19a, 19b that are moulded from a rigid plastics material and press-fitted together.

Each blade 19 includes a light 21 in a forward end of the blade to assist a doctor viewing a larynx of a patient.

The laryngoscope is constructed so that the lights 21 are actuated automatically as the blade assemblies 15 are folded outwardly from the storage position shown in FIG. 5 to the operative position shown in FIG. 4.

Typically, each sleeve (not shown) is in the form of a member that is moulded from a suitable clear plastics material and is shaped to define a suitable hand-grip.

As can best be seen from the exploded perspective view of FIG. 6, the ends of the blade assemblies 19 that are pivotally connected together are formed to define the hub 17. The hub 17 also includes two complementary shaped cylindrical sleeves 37 that are located between the ends of the blade assemblies 19. The four components are formed to be assembled together as a press fit.

As can best be seen from FIG. 6, the hub 17, and more particularly the sleeves 37, defines a hollow chamber that houses a battery or batteries (not shown) for powering the lights 21 of the blades 19.

In use, a doctor selects a required blade 19 for a given patient, folds the blade assemblies 15 outwardly from the storage position shown in FIG. 5 to the operative position shown in FIG. 4, removes the outer sleeve from the selected blade assembly 15 thereby exposing the blade 19, and grips the other blade assembly 15 as a handle of the laryngoscope. In this position, the doctor can then use the laryngoscope to assess a patient.

The laryngoscopes shown in FIGS. 1-6 are lightweight and compact units—comparable in size to conventional laryngoscopes.

The embodiment of the laryngoscope shown in FIGS. 1-3 is an effective instrument that can be carried conveniently by a doctor and quickly manipulated from a folded position to an operative position.

The embodiment of the laryngoscope shown in FIGS. 4-6 is also an effective instrument that that can be carried conveniently by a doctor and quickly manipulated from a folded position to an operative position and has an additional advantage of providing doctors with two blades 19 to select from. This is a significant advantage, particularly in crisis situations where time is important.

The laryngoscope of the present invention provides doctors with the possibility of conventional use with a reusable handle or with two blades 19 to select from and this is a significant advantage, particularly in crisis situations where time is important.

Many modifications may be made to the embodiments of the laryngoscope of the present invention shown in FIGS. 1-6 without departing from the spirit and scope of the present invention.

By way of example, whilst the blade assemblies 15 of the laryngoscope shown in FIGS. 4-6 includes outer sleeves, the present invention is not so limited and extends to any members that can protect the blades 19 of the assemblies and can be readily removed to allow use of the blades.

In addition, whilst the embodiments of the laryngoscopes shown in FIGS. 1-6 are made from rigid plastics materials, the present invention is not so limited and the laryngoscopes may be made from any suitable material.

In addition, whilst the embodiments of the laryngoscopes shown in FIGS. 1-6 are constructed so that the lights 7, 21 are actuated automatically as the blade 5 and the blade assemblies 15 are folded outwardly from the storage positions to the operative positions, the present invention is not so limited and extends to other arrangements. One example of another arrangement is switch-operated lights 7, 21.

The invention claimed is:

1. A laryngoscope that includes two blade assemblies, each assembly including a rigid blade that is adapted to be inserted into a larynx of a patient, wherein the blade of one of the two blade assemblies is larger than the blade of the other of the two blade assemblies to be suitable for different patients, the assemblies being pivotally connected together at one end of each assembly so that the assemblies can be folded relative to each other from a storage position in which the assemblies are in side by side relationship and extend generally in the same direction and an operative position in which the assemblies extend in different directions, whereby in use the blade of one assembly can be inserted into the larynx of the patient to allow an assessment of the patient to be made and the other assembly can operate as a handle and be gripped by a user to facilitate insertion of the blade of the one assembly into the larynx.

2. The laryngoscope defined in claim 1 wherein the blade assemblies extend at an angle of about 90° in the operative position.

3. The laryngoscope defined in claim 1 wherein each blade includes a light in a forward end to assist a user observing a patient.

4. The laryngoscope defined in claim 3 wherein the lights of the blades actuate automatically as the blade assemblies are folded outwardly from the storage position to the operative position.

5. The laryngoscope defined in claim 3 wherein the lights of the blades are actuated by switches on the blades.

6. The laryngoscope defined in claim 1 wherein the laryngoscope includes a hub that defines a pivotal mounting for the blade assemblies.

7. The laryngoscope defined in claim 6 wherein each blade includes a light in a forward end to assist a user observing a patient, and the hub defines a housing for a battery or batteries for the lights of the blade assemblies.

8. The laryngoscope defined in claim 7 wherein the lights of the blades actuate automatically as the blade assemblies are folded outwardly from the storage position to the operative position.

9. The laryngoscope defined in claim 7 wherein the lights of the blades are actuated by switches on the blades.

10. The laryngoscope defined in claim 1 wherein each blade is formed from two components that are molded from a rigid plastics material and press-fitted together.

11. The laryngoscope defined in claim 1 wherein each blade is curved along its length.

12. The laryngoscope defined in claim 1 wherein each blade has a first surface and a second surface spaced from opposite to the first surface such that in the storage position, the second surface of one blade is spaced from and faces the second surface of the other blade.

\* \* \* \* \*

UNITED STATES PATENT AND TRADEMARK OFFICE
CERTIFICATE OF CORRECTION

PATENT NO. : 9,078,614 B2
APPLICATION NO. : 12/374588
DATED : July 14, 2015
INVENTOR(S) : Ian John Bird It is certified that error appears in the above-identified patent and that said Letters Patent is hereby corrected as shown below:

On the Title Page

In the PCT Filed Date, Item (22): please delete "June 22, 2007", and replace it with "June 20, 2007".

Signed and Sealed this
Sixteenth Day of August, 2016

Michelle K. Lee
*Director of the United States Patent and Trademark Office*